United States Patent [19]

Kikuchi et al.

[11] Patent Number: 5,102,962
[45] Date of Patent: Apr. 7, 1992

[54] PHENOLIC POLYMER AND PRODUCTION THEREOF

[75] Inventors: Tohru Kikuchi; Hiroyuki Kawakami; Takayuki Saito, all of Hitachi, Japan

[73] Assignee: Hitachi Chemical Company, Ltd., Tokyo, Japan

[21] Appl. No.: 499,701

[22] Filed: Mar. 27, 1990

Related U.S. Application Data

[62] Division of Ser. No. 159,203, Feb. 23, 1988, Pat. No. 4,968,759.

[51] Int. Cl.$^5$ .............................................. C08G 61/64
[52] U.S. Cl. .................................... 525/534; 525/50; 525/390; 525/391; 528/86; 528/212

[58] Field of Search ................. 525/534, 390, 391, 50; 528/86, 212

[56] References Cited

U.S. PATENT DOCUMENTS 4,968,759 11/1990 Kikuchi et al. ..................... 525/534

Primary Examiner—Harold D. Anderson
Attorney, Agent, or Firm—Antonelli, Terry, Stout & Kraus

[57] ABSTRACT

A phenolic polymer obtained by reacting a phenolic compound with a bis(hydroxyalkyl)benzene, followed by alkylation of ortho positions or para position with respect to the hydroxyl group of the terminal phenol groups of the produced polymer is suitable for use as a heat resistant antioxidant for thermoplastic resins.

6 Claims, No Drawings

PHENOLIC POLYMER AND PRODUCTION THEREOF

This is a divisional application Ser. No. 07/159,203, filed Feb. 23, 1988.

BACKGROUND OF THE INVENTION

This invention relates to a phenolic polymer useful as an antioxidant and a process for producing the same.

As antioxidants, there has widely been used 2,6-ditertiary-butyl paracresol as a phenolic compound. But since it has a boiling point of 265° C., it volatilizes under kneading conditions (270°–350° C.) with a thermoplastic resin such as polypropylene. In order to prevent this, pentaerythrityl-tetrakis[3-(3,5-di-tert-butyl-4-hydroxyphenyl)propionate] and the like are used as an antioxidant for thermoplastic resins. Recently, with an increase of processing temperature of thermoplastic resins, for example, up to 350° C. in the case of engineering plastics, even the latter antioxidant volatilizes. For this reason, heat resistant phenolic antioxidants have been desired.

It is proposed in U.S. Pat. No. 3,004,953 to produce a special phenolic resin suitable as an antioxidant by reacting a phenol with para- or metadiisopropenylbenzene using an alkylation catalyst such as Brönsted acid or Lewis acid at 60° to 120° C. The molecular weight, structure and repeating units of the special phenolic resin are not disclosed therein, but when the phenol is used in excess in molar ratio to the para- or meta-diisopropenylbenzene, the phenol moiety is present at both ends of the resulting polymer. When used as an antioxidant, it is necessary to have substituents at both ortho positions of the phenol. When hydrogen is present at the ortho positions, the effect is reduced.

According to experiments of the present inventors after the process of said U.S. Pat. No. 3,004,593 using para-cresol and para-diisopropenylbenzene, it was found by gel permeation chromatography that a large amount of homopolymer of para-diisopropenylbenzene is produced in addition to an alkylation reaction product of para-diisopropenylbenzene with para-cresol, and at the same time a large amount of para-cresol is retained unreacted. This means that the polymer obtained by the process of U.S. Pat. No. 3,004,953 is a mixture of the alkylation reaction product and the homopolymer, and the amount of phenolic hydroxyl group per unit weight of the obtained resin is smaller than that obtained from calculation considering the amounts of the starting compounds.

Therefore, when the special phenolic resin of said U.S. patent is used as an antioxidant, a large amount of it should disadvantageously be added to thermoplastic resins in order to exhibit its effect.

On the other hand, it is proposed in U.S. Pat. No. 3,996,198 to produce a phenolic polymer by reacting a phenolic compound having hydrogens at both ortho positions with respect to a phenolic hydroxyl group with a diolefin compound by using a metallic aluminum to carry out the ortho-alkylation reaction. But since the ortho positions of terminal phenolic compound moieties of the resulting phenolic resin are not sealed, the effect as an antioxidant is little.

Further, it is also known crystalline cresol derivatives obtained by dehydration condensation of two molecules of cresol and one molecule of bis(1-hydroxy-1-methylethyl)benzene (Japanese Patent Unexamined Publication No. 58-121231) and crystalline alkyl-disubstituted phenol derivatives obtained by dehydration condensation of two molecules of alkyl-disubstituted phenol and one molecule of bis(1-hydroxy-1-methylethyl)benzene (Japanese Patent Unexamined Publication No. 58-121230). Since these cresol derivatives and alkyl-disubstituted phenol derivatives are crystalline monomeric compounds, there is a fundamental defect in that almost of these compounds volatilize under the kneading conditions with thermoplastic resins (270° to 350° C.).

SUMMARY OF THE INVENTION

It is an object of this invention to provide a heat resistant phenolic polymer useful as an antioxidant for thermoplastic resins and a process for producing the same.

This invention provides a phenolic polymer represented by the formula:

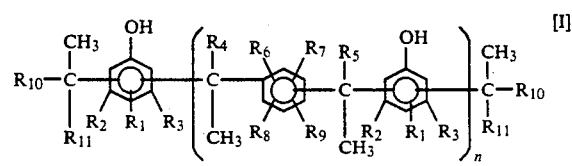

wherein $R_1$ is an alkyl group having 1 to 5 carbon atoms or an alkoxy group having 1 to 5 carbon atoms; $R_2$ and $R_3$ are independently hydrogen, an alkyl group having 1 to 5 carbon atoms or an alkoxy group having 1 to 5 carbon atoms; $R_4$ through $R_9$ are independently hydrogen, or an alkyl group having 1 to 5 carbon atoms; $R_{10}$ and $R_{11}$ are independently an alkyl group having 1 to 5 carbon atoms; and n is 2 or more and 75 or less in average.

This invention also provides a process for producing a phenolic polymer of the formula [I] which comprises reacting a phenolic polymer of the formula:

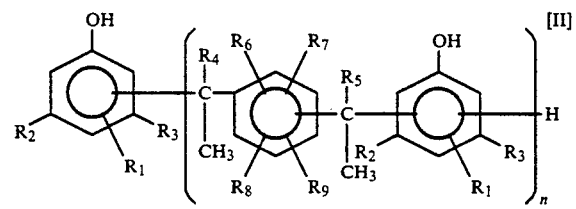

wherein $R_1$ through $R_9$ and n are as defined above, with at least one compound selected from the group consisting of

and

wherein $R_{10}$ and $R_{11}$ are as defined above, to carry out alkylation of ortho positions or para position with respect to the hydroxyl group of the terminal phenol groups of the phenolic polymer of the formula [II].

DESCRIPTION OF THE PREFERRED EMBODIMENTS

The starting phenolic polymer of the formula:

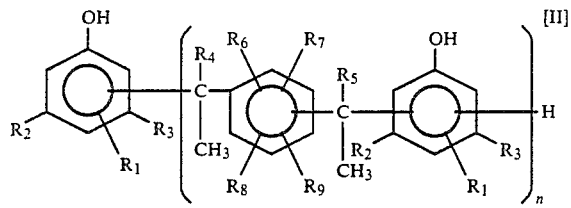

wherein $R_1$ is an alkyl group having 1 to 5 carbon atoms or an alkoxy group having 1 to 5 carbon atoms; $R_2$ and $R_3$ are independently hydrogen, an alkyl group having 1 to 5 carbon atoms or an alkoxy group having 1 to 5 carbon atoms; $R_4$ through $R_9$ are independently hydrogen, or an alkyl group having 1 to 5 carbon atoms; and n is 2 or more and 75 or less in average, can be produced by reacting a phenolic compound of the formula:

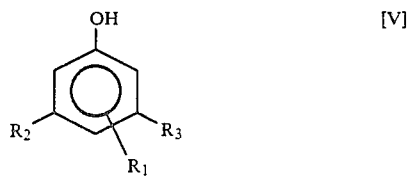

wherein $R_1$, $R_2$ and $R_3$ are as defined above, with a bis(hydroxyalkyl)benzene compound of the formula:

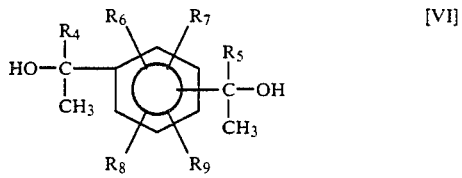

wherein $R_4$ through $R_9$ are as defined above, in the presence of an alkylation catalyst.

Examples of the phenolic compound of the formula [V] are o-cresol, p-cresol, o-methoxyphenol, p-methoxyphenol, o-ethylphenol, p-ethylphenol, o-propylphenol, p-propylphenol, o-butylphenol, p-butylphenol, o-amylphenol, p-amylphenol, o-cyclopentylphenol, p-cyclopentylphenol, 2,3-dimethylphenol, 3,4-dimethylphenol, 2,5-dimethylphenol, 3-methoxy-2-methylphenol, 3-methoxy-4-methylphenol, 2,3,5-trimethylphenol, 3,4,5-trimethylphenol, etc. These phenolic compounds can be used alone or as a mixture thereof.

It is necessary to use a phenolic compound having a hydrogen atom at two positions among three positions of the ortho positions and the para position with respect to the phenolic hydroxyl group, since two alkylation reaction sites are necessary to produce a linear phenolic polymer without gelation by alkylation reaction of the bis(hydroxyalkyl)benzene.

Examples of the bis(hydroxyalkyl)benzene compound of the formula [VI] are m-bis(1-hydroxy-1-methylethyl)benzene, p-bis(1-hydroxy-1-methylethyl)benzene, m-bis(1-hydroxyethyl)benzene, p-bis(1-hydroxyethyl)benzene, n-bis(1-hydroxyl-1-methylpropyl)benzene, p-bis(1-hydroxy-1-methylpropyl)benzene, etc. These compounds can be used alone or as a mixture thereof. Among them, m-bis(1-hydroxy-1-methylethyl)benzene and p-bis(1-hydroxy-1-methylethyl)benzene of the formula:

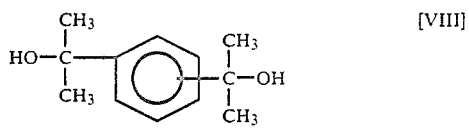

wherein the two hydroxyisopropyl groups are bonded to the meta positions or para position, alone or as a mixture thereof, are preferable.

The catalyst used for the synthesis of the phenolic polymer of the formula [II] is preferably an alkylation catalyst. It is possible to use a cationic ion exchange resin, zeolite, a solid acid such as silica-alumina, etc., as the catalyst. Since to carry out the reaction in a homogeneous system is easier than in a heterogeneous system from the view point of handling, it is preferable to use a Brönsted acid such as a mineral acid, e.g., sulfuric acid, hydrochloric acid, phosphoric acid, etc., para-taluenesulfonic acid, etc., or a Lewis acid such as boron trifluoride, a complex of boron trifluoride, etc.

The alkylation catalyst is preferably used in an amount of 0.2 to 10% by weight based on a total weight of the phenolic compound and the bis(hydroxyalkyl)benzene compound. If the amount is too small, it takes a longer reaction time, while if the amount is too much, the removal of the catalyst after the reaction becomes complicated.

In the synthesis of the phenolic polymer of the formula [II], it is preferable to use 0.67 mole or more to less than 1.00 mole of the bis(hydroxyalkyl)benzene compound of the formula [VI] per mole of the phenolic compound of the formula [V]. If the amount of the compound [VI] is too small, e.g., less than 0.67 mole, unreacted phenolic compound [V] is retained too much and the amount of the molecule of the formula [II] wherein n=1 undesirably increases. On the other hand, if the amount of the compound [VI] is too much, e.g., more than 1.0 mole, no terminal groups due to the phenolic compound are present, but only hydroxyl terminals are undesirably retained.

Further, in the above-mentioned reaction, the phenolic compound and the bis(hydroxyalkyl)benzene compound can be added dividedly, so long as the total amounts are within the above-mentioned amounts.

In order to prevent volatilization of the phenolic polymer of the formula [I] at the time of kneading with an engineering plastic or molding thereof, it is preferable to make the molecular weight of phenolic polymer [I] sufficiently high, for example, to make n 3 or more in average. For this purpose, it is preferable to use 0.80 mole or more and less than 1.0 mole of the bis(hydroxyalkyl)benzene compound [VI] per mole of the phenolic compound [V].

The reaction of the compound [V] with the compound [VI] is preferably carried out at 60° to 130° C. If the reaction temperature is too low, the reaction rate becomes slow, while if the reaction temperature is too high, the resulting phenolic polymer [II] is easily colored. Since water is produced with the progress of the reaction, it is preferable to carry out the reaction at an azeotropic temperature of water and a solvent used.

As the solvent, there can be used paraffin series solvents such as n-hexane, cyclohexane, etc.; ketone series solvents such as acetone, methyl ethyl ketone, etc.;

alcohol series solvents such as methanol, ethanol, etc.; aromatic solvents such as benzene, toluene, xylene, chlorobenzene, etc., alone or as a mixture thereof. As mentioned above, it is preferable to use a solvent which can form an azeotropic composition with water, can dissolve the polymer produced and does not pertain to the reaction by itself. As such a solvent, the use of aromatic solvents such as benzene, toluene, xylene, chlorobenzene, etc. is preferable.

The phenolic polymer of the formula [II] thus obtained is a polymer having at least two repeating units represented by the parentheses in the formula [II] and does not contain a homopolymer of the alkylating agent. This is because the double bond of diisopropenylbenzene is highly reactive and brings about polymerization of double bonds each other in addition to the alkylation reaction at 60° C. or higher, but the bis(hydroxyalkyl)benzene used in this invention is a bifunctional alcohol containing no double bond and does not cause homopolymerization substantially under the reaction conditions used in this invention mentioned above.

The phenolic polymer of the formula [II] is then subjected to alkylation of ortho positions or para position with respect to the hydroxyl group of the terminal phenol groups with at least one compound selected from the group consisting of

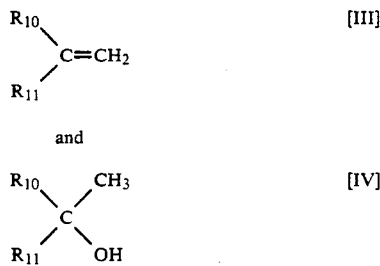

and wherein $R_{10}$ and $R_{11}$ are independently an alkyl group having 1 to 5 carbon atoms, to yield the phenolic polymer of the formula:

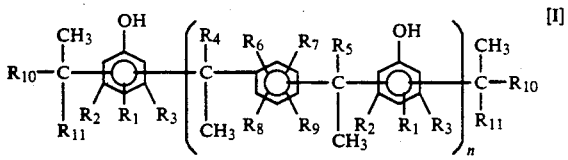

wherein $R_1$ through $R_{11}$ and n are as mentioned above. The alkylation reaction selectively takes place at the ortho positions or the para position.

Examples of the compound of the formula [III] are 2-methyl-1-propene, 2-methyl-1-butene, 2,4,4,-trimethyl-1-pentene, etc. Among them, 2-methyl-1-propene is more preferable.

Examples of the compound of the formula [IV] are t-butyl alcohol, t-amyl alcohol, 2,4,4-trimethyl-2-pentanol, etc. Among them, t-butyl alcohol is more preferable.

The terminal alkylation reaction is preferably carried out subsequent to the synthesis of the phenolic polymer of the formula [II]. In such a case, it is preferable to use 2 to 5 moles of the compound of the formula [III] or [IV] per mole of the phenolic polymer of the formula [II]. The average molar number of the phenolic polymer of the formula [II] is equal to difference in molar number between the phenolic compound [V] and the bis(hydroxyalkyl)benzene compound [VI].

If the amount of the compound [III] or [IV] is too small, the hydrogen bonded to one position of ortho and para positions with respect to the hydroxyl group of the terminal phenol groups of the phenolic polymer [II] is not alkyl substituted completely, while if the amount is too much, the amount of unreacted compound [III] or [IV] increases.

As the catalyst, the same catalyst as used in the alkylation reaction mentioned above can be used preferably in an amount of 0.2 to 10% by weight based on the weight of the polymer [II]. When the phenolic polymer [I] is produced successively after the synthesis of the polymer [II], since the alkylation catalyst used therein is retained, it is not necessary to newly add the catalyst into the reaction system.

The reaction of the polymer [II] with the compound [III] and/or [IV] is preferably carried out at 60° to 130° C. When the compound [III] is used, the reaction temperature of 60° to 90° C. is preferable in order to prevent the homopolymerization. The reaction time is preferably 1 to 5 hours.

After the reaction, the reaction solution is subjected to after-treatment such as a method of washing or neutralization washing with water and a dilute (1–2%) alkaline washing solution of sodium hydroxide, potassium hydroxide, sodium carbonate, sodium bicarbonate, or the like, a method of adding an alkaline powder of sodium bicarbonate, magnesium oxide, or the like, stirring and filtering the neutralized salt, or a method of adding an amine such as triethylamine, triethanolamine, morpholine, or the like for neutralizing the catalyst. The reaction solution from which the catalyst is removed by neutralization and washing with water, or removed by filtration after neutralization, or the reaction solution after neutralization is subjected to heating under reduced pressure to remove the reaction solvent, remaining the compound of the formula [III] or [IV] and to separate the phenolic polymer of the formula [I]. When trace amounts of the remaining monomers and oligomers are found by analysis, it is preferable to reprecipitate the phenolic polymer [I] from a poor solvent for the polymer such as an alcoholic solvent, e.g. methanol, ethanol, or the like, or a paraffin series solvent, e.g. hexane, cyclohexane, or the like.

The thus obtained phenolic polymer of the formula [I] is a colorless or pale yellow amorphous resinous material wherein n in the formula [I] is 2 or more and 75 or less in average based on the number average molecular weight. The molecular weight of the polymer [I] is in a range of 696 to 69,000 in number average molecular weight, depending on the starting materials used. For example, when cresol, bis(1-hydroxy-1-methylethyl)benzene and α-methylstyrene or hydroxyisopropylbenzene are used as the starting materials, the molecular weight becomes 752 to 20,000 in number average molecular weight.

From the viewpoint of volatility, the value of n in the phenolic polymer of the formula [IV] is preferably 3 or more in average based on the number average molecular weight. In this case, the number average molecular weight of the phenolic polymer becomes 934 or more.

In order to prevent blocking during storage, it is preferable to make the softening point of the phenolic polymer [I] 70° C. or higher. Further, from the viewpoint of compatibility with other resins or rubbers, the phenolic polymer wherein n in the formula [I] is 3 to 30 in average is particularly preferable.

The phenolic polymer of the formula [I] is clearly different from the cresol derivatives (Japanese Patent Unexamined Publication No. 58-121231) and the alkyl disubstituted phenol derivatives (Japanese Patent Unexamined Publication No. 58-121230) in that the latter two are bifunctional phenolic monomers and crystalline compounds, while the former (this invention) is a polymer having a higher molecular weight and an amorphous resinous material. Further, the reaction conditions for producing the above-mentioned derivatives and polymer are quite different. For example, in the case of the cresol derivatives or alkyl disubstituted phenol derivatives, cresol or alkyl disubstuted phenol should be used in a large excess amount such as 2.0 to 10 moles, preferably 2.0 to 6 moles per mole of bis(1-hydroxy-1-methylethyl)benzene.

The phenolic polymer of the formula [I] is useful as a heat resistant antioxidant for thermoplastic resins.

This invention is illustrated by way of the following Examples.

EXAMPLE 1

In a 1000-ml three-necked flask made of glass equipped with a Dean-Stark trap, 108 g (1.00 mole) of p-cresol, 184 g (0.95 mole) of m-bis(1-hydroxy-1-methylethyl)benzene, 150 g of toluene and 7.5 g of p-toluenesulfonic acid were placed and heated with stirring. When the temperature in the flask became 95° C., water began to be distilled together with toluene. The reaction was continued for 8 hours while maintaining the temperature in the flask at 105° C. The amount of water distilled was 34 ml. It was admitted that the m-bis(1-hydroxy-1-methylethyl)benzene was almost completely reacted. Then, the temperature of flask was lowered to 70° C. and 11.1 g (0.15 mole) of t-butyl alcohol was added to the flask, followed by stirring for 3 hours.

After completion of the reaction, the reaction solution in the flask was transferred to a separatory funnel and 150 g of toluene was added thereto. The p-toluenesulfonic acid was removed by washing with deionized water five times. The toluene solution was treated with an evaporator to remove 150 g of toluene, followed by pouring into 500 ml of methanol with stirring to give a white precipitate. The precipitate was dried under reduced pressure to yield 215 g of a white powder. The analysis by gel permeation chromatography revealed that the white powder was a polymer having a number average molecular weight of 1800 in terms of standard polystyrene. The resulting polymer was represented by the formula:

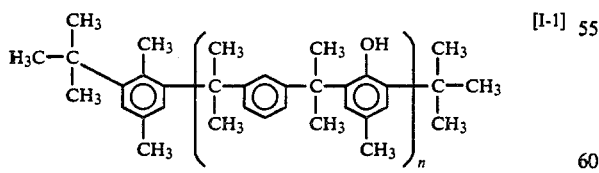
[I-1]

Thus, the value of n in the formula [I-1] became 5.9 in average.

The weight average molecular weight was 2,550, which means that the value in the formula [I-1] becomes 8.8 in average.

The softening point measured by a ring and ball softening point measuring apparatus was 135° C. Further, heat resistance of the polymer was evaluated by thermogravimetric analysis. When a sample was heated in the air at a temperature rise rate of 10° C./min, the weight loss began at 325° C. The proportion of weight loss at 350° C. was 2.5% by weight. This means that the phenolic polymer has good heat resistance and can be used sufficiently as a antioxidant for engineering plastics.

EXAMPLE 2

The steps until the reaction between p-cresol and m-bis(1-hydroxy-1-methylethyl)benzene were carried out in the same manner as described in Example 1, followed by blowing 2-methyl-1-propene into the reaction solution at a rate of 1.2 liters/hr (at 20° C.) for 3 hours with stirring. The charged amount of 2-methyl-1-propene was 8.4 g (0.15 mole). Then, the washing with water, and the solvent removal were conducted in the same manner as described in Example 1 to yield 210 g of a white precipitate (polymer) represented by the formula [I-1].

The high-performance liquid chromatography of the resulting polymer revealed that the number average molecular weight was 1600 in terms of standard polystyrene, the weight average molecular weight was 2,400. The softening point measured by the ring and ball softening point measuring apparatus was 130° C.

EXAMPLE 3

The process of Example 1 was repeated except for using o-cresol in place of p-cresol to yield a white powdery polymer represented by the formula:

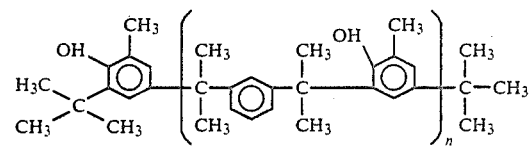

and/or

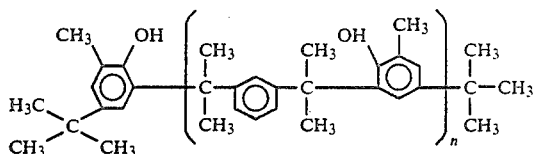

The resulting polymer had a number average molecular weight of 2,050 and a weight average molecular weight of 3,970.

EXAMPLE 4

The process of Example 1 was repeated except for using p-bis(1-hydroxy-1-methylethyl)benzene in place of m-bis(1-hydroxy-1-methylethyl)benzene to yield a white powdery polymer represented by the formula:

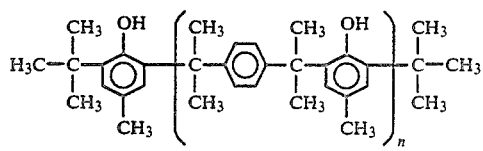

The resulting polymer had a number average molecular weight of 1,850, a weight average molecular weight of 2,940, a softening point of 135° C. and a weight loss beginning temperature of 330° C. by the thermogravimetric analysis.

EXAMPLE 5

The process of Example 1 was repeated except for using p-bis(1-hydroxy-1-methylethyl)benzene in place of m-bis(1-hydroxy-1-methylethyl)benzene to yield a white powdery polymer represented by the formula:

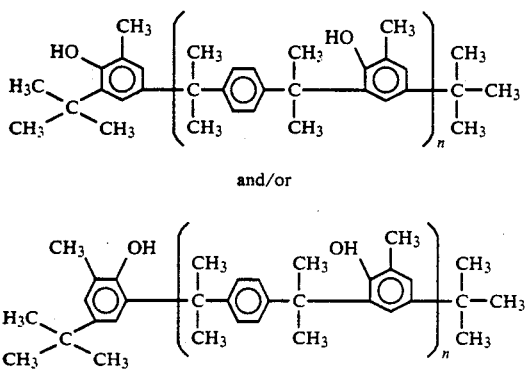

and/or

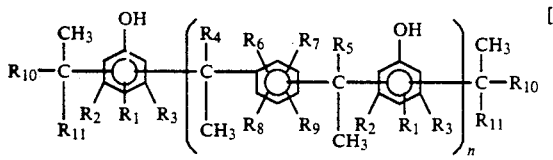

The resulting polymer had a number average molecular weight of 1,900 and a weight average molecular weight of 3,200.

What is claimed is:

1. A process for producing phenolic polymer represented by the formula:

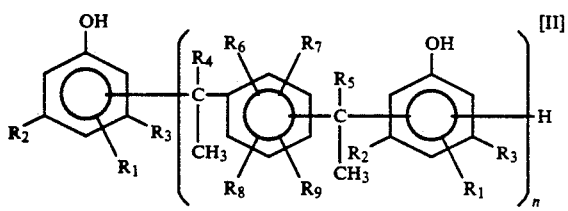

wherein $R_1$ is an alkyl group having 1 to 5 carbon atoms or an alkoxy group having 1 to 5 carbon atoms; $R_2$ and $R_3$ are independently hydrogen, an alkyl group having 1 to 5 carbon atoms or an alkoxy group having 1 to 5 carbon atoms; $R_4$ through $R_9$ are independently hydrogen, or an alkyl group having 1 to 5 carbon atoms; $R_{10}$ and $R_{11}$ are independently an alkyl group having 1 to 5 carbon atoms; and n is 2 to 75 in average, which comprises reacting a phenolic polymer of the formula:

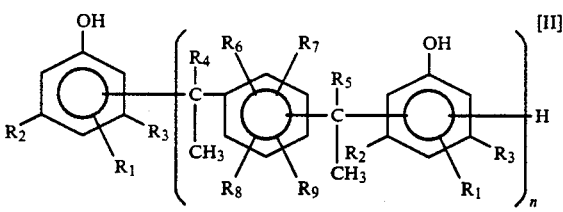

wherein $R_1$ through $R_9$ and n are as defined above, with at least one compound selected from the group consisting of a compound of the formula:

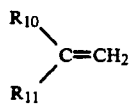

or a mixture of the compound of formula [III] and a compound of the formula:

wherein $R_{10}$ and $R_{11}$ are as defined above, to carry out alkylation of ortho positions or para position with respect to the hydroxyl group of the terminal phenol groups of the phenolic polymer of the formula [II].

2. A process according to claim 1, wherein the compound of the formula [III] is 2-methyl-1-propene, 2-methyl-1-butene, 2,4,4-trimethyl-1-pentene or a mixture thereof, and the compound of the formula [IV] is t-butyl alcohol, t-amyl alcohol, 2,4,4-trimethyl-2-pentanol or a mixture thereof.

3. A process according to claim 1, wherein the phenolic polymer of the formula [II] is reacted with the at least one compound of the formula [III].

4. A process according to claim 3, wherein the compound of the formula [III] is 2-methyl-1-propene, 2-methyl-1-butene, 2,4,4-trimethyl-1-pentene or a mixture thereof.

5. A process for producing phenolic polymer represented by the formula:

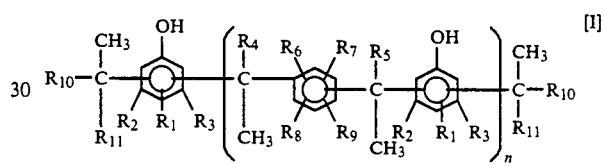

wherein $R_1$ is an alkyl group having 1 to 5 carbon atoms or an alkoxy group having 1 to 5 carbon atoms; $R_2$ and $R_3$ are independently hydrogen, an alkyl group having 1 to 5 carbon atoms or an alkoxy group having 1 to 5 carbon atoms; $R_4$ through $R_9$ are independently hydrogen, or an alkyl group having 1 to 5 carbon atoms; $R_{10}$ and $R_{11}$ are independently an alkyl group having 1 to 5 carbon atoms; and n is 2 to 75 in average, which comprises reacting a phenolic polymer of the formula:

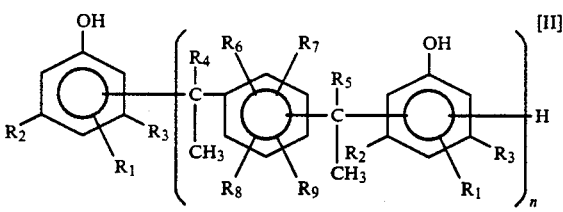

wherein $R_1$ through $R_9$ and n are as defined above, with at least one compound of the formula:

wherein $R_{10}$ and $R_{11}$ are as defined above, to carry out alkylation of ortho positions or para position with respect to the hydroxyl group of the terminal phenol groups of the phenolic polymer of the formula [II].

6. A process according to claim 5, wherein the compound of the formula [III] is 2-methyl-1-propene, 2-methyl-1-butene, 2,4,4-trimethyl-1-pentene or a mixture thereof.

* * * * *